United States Patent [19]

Gross et al.

[11] Patent Number: 5,637,318
[45] Date of Patent: Jun. 10, 1997

[54] DERMATOLOGICAL AGENT FOR ASSISTING THE TRANSPORT OF OXYGEN IN THE SKIN

[75] Inventors: Udo Gross, Berlin; Joachim Röding, Wiesbaden, both of Germany; Klaus Stanzl, White Plains, N.Y.; Leonhard Zastrow, Monaco, Monaco

[73] Assignee: Lancaster Group AG, Ludwigshafen, Germany

[21] Appl. No.: 674,850

[22] PCT Filed: Jun. 24, 1993

[86] PCT No.: PCT/DE93/00572

§ 371 Date: Dec. 22, 1994

§ 102(e) Date: Dec. 22, 1994

[87] PCT Pub. No.: WO94/00109

PCT Pub. Date: Jan. 6, 1994

Related U.S. Application Data

[63] Continuation of Ser. No. 360,847, Dec. 22, 1994, abandoned.

[30] Foreign Application Priority Data

Jun. 26, 1992 [DE] Germany ............ 42 21 268.5

[51] Int. Cl.$^6$ ............... A61K 9/127; A61K 7/00
[52] U.S. Cl. ............. 424/450; 424/401; 424/43; 424/45; 264/4.1; 264/4.3; 514/944; 514/969
[58] Field of Search ............. 424/450, 401, 424/43, 45; 264/4.1, 4.3; 514/944, 969

[56] References Cited

U.S. PATENT DOCUMENTS

| | | | |
|---|---|---|---|
| 4,366,169 | 12/1982 | White | 424/285 |
| 4,569,784 | 2/1986 | Moore | 252/315.1 |
| 5,061,484 | 10/1991 | Heldebrant | 424/78 |
| 5,160,669 | 11/1992 | Wallach et al. | 264/43 |
| 5,204,112 | 4/1993 | Hope | 424/450 |
| 5,219,538 | 6/1993 | Henderson | 428/402.2 |
| 5,246,703 | 9/1993 | Durfee | 424/401 |

FOREIGN PATENT DOCUMENTS

| | | |
|---|---|---|
| 0069307 | 1/1983 | European Pat. Off. . |
| 0091313 | 10/1983 | European Pat. Off. . |
| 0105584 | 4/1984 | European Pat. Off. . |
| 0 296 661 | 12/1988 | European Pat. Off. . |
| 41 27 442 | 2/1993 | Germany . |
| 8900848 | 2/1989 | WIPO . |
| 89/08459 | 9/1989 | WIPO . |
| 91/00110 | 1/1991 | WIPO . |
| 91/16068 | 10/1991 | WIPO . |
| 92/06676 | 4/1992 | WIPO . |

OTHER PUBLICATIONS

Lautenschlager in cosmetics & toiletries 105, May 1990.

*Primary Examiner*—Gollamudi S. Kishore
*Attorney, Agent, or Firm*—Collard & Roe, P.C.

[57] ABSTRACT

The invention relates to a dermatological agent for assisting the transport of oxygen in the skin, a process for its preparation and the use thereof. The problem with the known dermatological agents is the inadequate supply of oxygen to the skin and the adjoining tissue. The object of the invention is therefore to get through the horny layer of the skin and the epidermis by penetration processes in order to increase the oxygen concentration in the dermal area and adjoining tissue and to activate metabolic processes. According to the invention, this is effected by means of a dermatological agent containing asymmetric lamellar aggregates, consisting of phospholipids and oxygen-laden fluorocarbon or fluorocarbon mixture, the amount of fluorocarbon being in the range from 0.2 to 100% weight/volume, in a carrier which is suitable for dermatological use. Preparation is effected by emulsification of the corresponding constituents, and use in ointments, creams, lotions, waters, alcoholic extracts, pastes, powders, gels, tinctures or on dressings and plasters or in a spray.

18 Claims, 2 Drawing Sheets

DERMATOLOGICAL AGENT FOR ASSISTING THE TRANSPORT OF OXYGEN IN THE SKIN

This is a continuation of application Ser. No. 08/360,847 filed on Dec. 22, 1994 now abandoned.

The invention relates to a dermatological agent which penetrates into the dermal area of the skin and adjoining tissue and produces an improved supply of oxygen in this region.

U.S. Pat. No. 4,366,169 (White) claims the use of fluorocarbons for the treatment of skin injuries and wounds, in particular of burns. In this case the oxygen-containing fluorocarbon is put onto the skin, or onto appropriate dressings or similar means either directly or as an emulsion. U.S. Pat. No. 4569784 (Moore) describes the preparation of a gel with gas transport properties for use on the skin. The complicated process consists in emulsifying a water-immiscible organic liquid, e.g. a fluorocarbon, in the presence of an emulsifier by an emulsification process. A concentration process follows (e.g. ultra-centrifugation, ultrafiltration), which leads to the formation of a gel phase. In the third step which then follows, the separation of the clear liquid from the pasty solid (gel phase) is effected by decantation, filtration or evaporation. This gel is applied to the skin in suitable formulations, and it acts there without, however, penetrating the horny layer.

EP-A-296661 (Borgarello) describes a fluorocarbon-containing single phase system which can act as an isotropic or anisotropic formulation in the cosmetic field and also as a dermatological agent as an oxygen transporter. In this case, fluorocarbons having a maximum concentration of 50% are emulsified in water with perfluorinated emulsifiers of the alkanesulphonamide type in the presence of an aliphatic alcohol as an auxiliary emulsifier.

WO-A-08 459 describes a perfluorcarbon emulsion containing phospholipid vesicles as a blood substitute in which the phospholipid monomers are polymerised. In WO-A-91 00110, fluorcarbon emulsions containing phospholipids are disclosed in which the phospholipids has saturated carbon bonds. From WO-A-92 06676, oil-filled only slightly lamellar vesicles composed of phospholipids are known, whose structure corresponds to the customary vesicle structure. In the known processes described, the compositions described, which contain fluorocarbons, act on the skin in a system-related manner at the site of their application.

The present invention is based on the object of getting through the horny layer of the skin and the epidermis by penetration processes, in order to increase the oxygen concentration in the dermal area and the tissue adjoining it and to activate metabolic processes.

According to the invention, the dermatological agent for assisting the transport of oxygen in the skin consists of asymmetric lamellar aggregates which are constructed from phospholipids laving a phosphatidylcholine content of 30 to 99% by weight which in their core, in contrast to the well-known aqueous lipisomes, contain fluorocarbons or mixtures thereof. The dermatological agent according to the invention thus consists of asymmetric lamellar aggregates which consist of phospholipids having a phosphatidylcholine content of 30 to 99% by weight and oxygen-laden fluorocarbon or fluorocarbon mixture, the amount of fluorocarbon being in the range from 1 to 100% w/v (w/v= weight/volume), in a carrier which is suitable for dermatological use.

The lamellar aggregates are able, because of their phospholipid structure, which is structurally and chemically very similar or is partly identical to the cell membranes, and in combination with their aggregate size, which can be controlled during preparation, to penetrate into deeper-lying skin layers and to become active there. This takes place in contrast to the invention descriptions mentioned in the prior art, which do not permit the transport of the fluorocarbons into deeper-lying regions of the skin. The known processes are ineffective in respect of the claimed effect.

A plurality of fluorocarbons can be employed, e.g. aliphatic straight-chain and branched fluoroalkanes, mono- or bicyclic and optionally fluoroalkyl-substituted fluorocycloalkanes, perfluorinated aliphatic or bicyclic amines, bis(perfluoroalkyl)ethenes or mixtures thereof. Particularly preferred fluorocarbons are those such as perfluorodecalin, F-butyltetrahydrofuran, perfluorotributylamine, perfluorooctyl bromide, bis-fluoro (butyl)-ethene or bis-fluoro(hexyl)ethene or $C_6$-$C_9$-perfluoroalkanes.

The amount of fluorocarbons in this case is in the range from 1 to 100% w/v, preferably in the range from 40 to 100%. A particularly preferred range is that from 70 to 100% w/v.

The phospholipids employed according to the invention are natural phospholipids such as soya lecithin and egg lecithin, and also synthetic phospholipids. In these phospholipids, the content of phosphatidylcholine is in the range from 30 to 99% by weight, in particular 70 to 99% by weight, i.e. phospholipids laving high phosphatidyl contents are preferred.

In addition to phosphatidylcholine, lysolecithins can also be present in the concentration range from 0.1 to 10% by weight and/or charged phospholipids such as phosphatidylethanolamine, n-acetylphosphatidylethanolamine or phosphatidic acid in the concentration range 0.1 to 30% by weight.

In contrast to the known aqueous liposomes (vesicles), the phospholipid-stabilised aggregates according to the invention carry hydrophobic fluorocarbons in their core, which are capable of the transport of oxygen. Their interfacial chemical stabilisation is effected primarily by a monolayer with inverse arrangement and secondarily by a structure of bilayer films attached thereto. According to the invention, the asymmetric lamellar aggregates therefore always have at least one three-layer structure, in contrast to the known two-layer vesicles. Because of the peculiarity of their structural arrangement, these novel aggregates are designated as asymmetric lamellar oxygen carriers. Their exceptional colloid-chemical stability can presumably be traced back to the lamellar structure and to the surface charge of the aggregates. The latter can be traced back to the choice of suitable phosphalipids or mixtures thereof of natural as well as of synthetic origin. Primarily, phospholipids, in particular phosphatidylcholine in the said concentration range from 30 to 99% optionally in combination with lysolecithins of concentration from 0.1 to 10% and/or charged phospholipids in the concentration range 0.1 to 30% by weight are responsible for an advantageous action in this sense. The claimed action of the phospholipids is verified by corresponding negative zeta potentials and by the measurement of charge densities (on titration with a cationic polyelectrolyte).

It was possible to determine the dependence of the penetration rate and the depth of penetration of the particle size of the aggregates experimentally by separate investigations in animal experiments using labelled encapsulated fluorocarbons. According to these experiments, relatively small particles migrate more rapidly and more deeply into the skin tissue than relatively large particles. The choice of fluorocarbons or mixtures thereof according to their lipid solubility (represented by their critical solubility temperature CST in n-hexane) permits, as a further important criterion, the regulation of the residence time in the tissue. While, e.g. perfluorotributylamine (F-TBA, CST 59° C.), with a high CST value and poor lipid solubility has a relatively large residence time, in contrast to this perfluorodecalin (PFD, CST 22° C.), but also F-butyltetrahydrofuran, F-hexane and others are released correspondingly more rapidly from the tissue. With the aid of fluorocarbon mixtures, systems can be prepared specifically with the desired CST values, i.e. lipid and membrane solubilities with respect to the intended use.

The content of the fluorocarbons as oxygen carriers in the lamellar aggregates can vary between 1 and 100% w/v according to the intended application. Suitable fluorocarbons are in particular: aliphatic straight-chain and branched alkanes laving 6 to 12 carbon atoms, e.g. perfluorohexane, perfluorononane; mono- or bicyclic cycloalkanes which are optionally F-alkyl-substituted, e.g. perfluoromethylcyclohexane, perfluorodecalin; aliphatic tertiary amines, n-containing polycycles, e.g. perfluorotripropylamine, perfluorotributylamine; perfluoroethers, such as aliphatic ethers and polyethers, F-alkylfurans, bicyclic and substituted bicyclic ethers having 2 or 3 oxygen atoms in the molecule, e.g. perfluorodihexyl ether, perfluorobutyltetrahydrofuran; perfluoroalkyl halides, e.g. perfluorooctyl bromide, perfluorohexyl bromide, perfluorooctyl chloride; bis-F(alkyl)ethenes, e.g. bis-F(butyl)ethene, bis-F(hexyl)ethene.

The term "fluorocarbons" used here is understood as meaning perfluorinated or highly fluorinated carbon compounds or mixtures which are able to transport gases such as $O_2$ and $CO_2$. Highly fluorinated hydrocarbon compounds within the meaning of this invention are those in which most of the hydrogen atoms are replaced by fluorine atoms, e.g. the bis-F(alkyl)ethenes which, as far as can be detected, are chemically and biologically inert and thus non-toxic. This is usually achieved if approximately up to 90% of the hydrogen atoms are replaced by fluorine atoms. Preferred fluorocarbons within the meaning of the present invention are those in which at least 95% of the hydrogen atoms are replaced, more preferably 98% and most preferably 100%.

Individual fluorine atoms can also be replaced by other halogen atoms such as bromine or chlorine.

Suitable phospholipids are naturally occurring phospholipids such as soya or egg lecithin, and also lecithins (phospholipids) which can be prepared synthetically, which overall are known to be skin-compatible. Because of the advantageous action on the stability of the asymmetric lamellar aggregates, phospholipid mixtures having a content of 30 to 99% of phosphatidylcholine in addition to other naturally occurring accompanying products are preferably used. The phospholipid content in the dermatological formulation varies between 0.5 and 20, preferably 10 to 20%.

The invention also relates to a process for the preparation of a phospholipid-containing dermatological agent, which consists in emulsifying phospholipids having a phosphatidylcholine content of 30 to 99% by weight with a fluorocarbon or a fluorocarbon mixture which is laden with oxygen, the amount of fluorocarbon being in the range from 0.2 to 100% w/v, and incorporating the asymmetric lamellar aggregates having a particle size from 50 to 1000 nm obtained in this way into a carrier which is suitable for dermatological use. Emulsification is effected in the presence of water and optionally with the addition of monohydric or polyhydric aliphatic alcohols. Emulsification can also be effected by preemulsification of the crude dispersion by addition of the fluorocarbon to an aqueous phospholipid solution at a temperature corresponding to the starting substances employed. The preemulsification is appropriately effected at relatively high speeds of rotation, e.g. 12,000 to 15,000 rpm. The actual homogenisation is then effected in a high-pressure homogeniser. The homogenisation can also be effected using other known processes, for example ultrasound. The degree of energy input into the disperse system turns out to be indirectly proportional to the particle sizes.

Heat-sterilisation in an autoclave is possible without an effect on the particle sizes. To avoid autoxidation processes in the unsaturated fatty acid radical of native lipids, antioxidants, e.g. α-tocopherol can be added.

The use of phospholipids having high phosphatidylcholine contents is particularly advantageous. These are in general between 10 and 99% by weight, preferably 30 to 99% by weight, in particular 70 to 99% by weight.

The fluorocarbons used are the abovementioned fluorocarbons or fluorocarbon mixtures in the limits indicated for these. With the aid of their known $O_2$ solubilities, the vapour pressure and the critical solubility temperature, the loading with oxygen and the depth of penetration can be adjusted by a person skilled in the art in a controlled manner.

The mode of action of the fluorocarbon-containing asymmetric lamellar aggregates is based on the release of oxygen to undersupplied tissue via a topical application. An efficient use is also conceivable for oxygen-undersupplied fatty tissue as well as for supplies which are deficient due to arteriosclerosis.

The incorporation of the asymmetric lamellar aggregates as active substance into ointments, creams, lotions and other aqueous or alcoholic dermatological formulations is effected depending on the intended use, it being possible to vary the fluorocarbon content and thus the $O_2$ availability within wide limits. The aggregates can be partially laden or saturated with gaseous oxygen before incorporation into all dermatological systems, e.g. gels, pastes, powders, ointments, creams and lotions. Even the saturation with the oxygen of the atmospheric air by means of the establishment of equilibrium which customarily takes place according to Henry's law offers a higher oxygen capacity than all comparable known systems.

The dermatological agent according to the invention can also be applied to dressings, plasters, wound coverings, and other agents coming into contact with the skin. For example, it can also be applied as a spray.

The invention will be illustrated in greater detail below by means of examples. In the associated drawings

Figure 1:
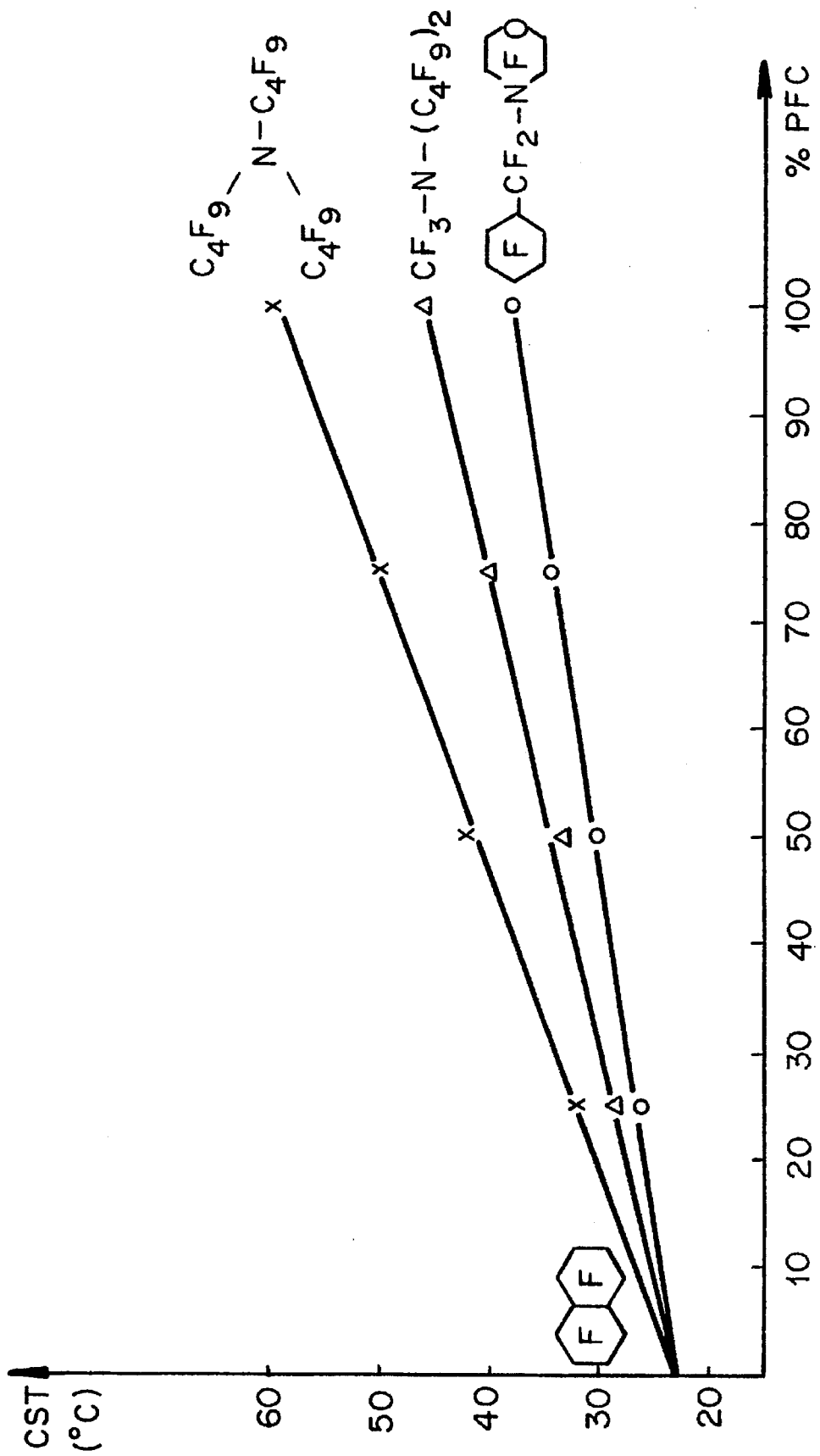
FIG. 1 is a diagram of the critical solubility temperatures (CST) of perfluorocarbon mixtures in n-hexane using perfluorodecalin as a starting point
Figure 2:
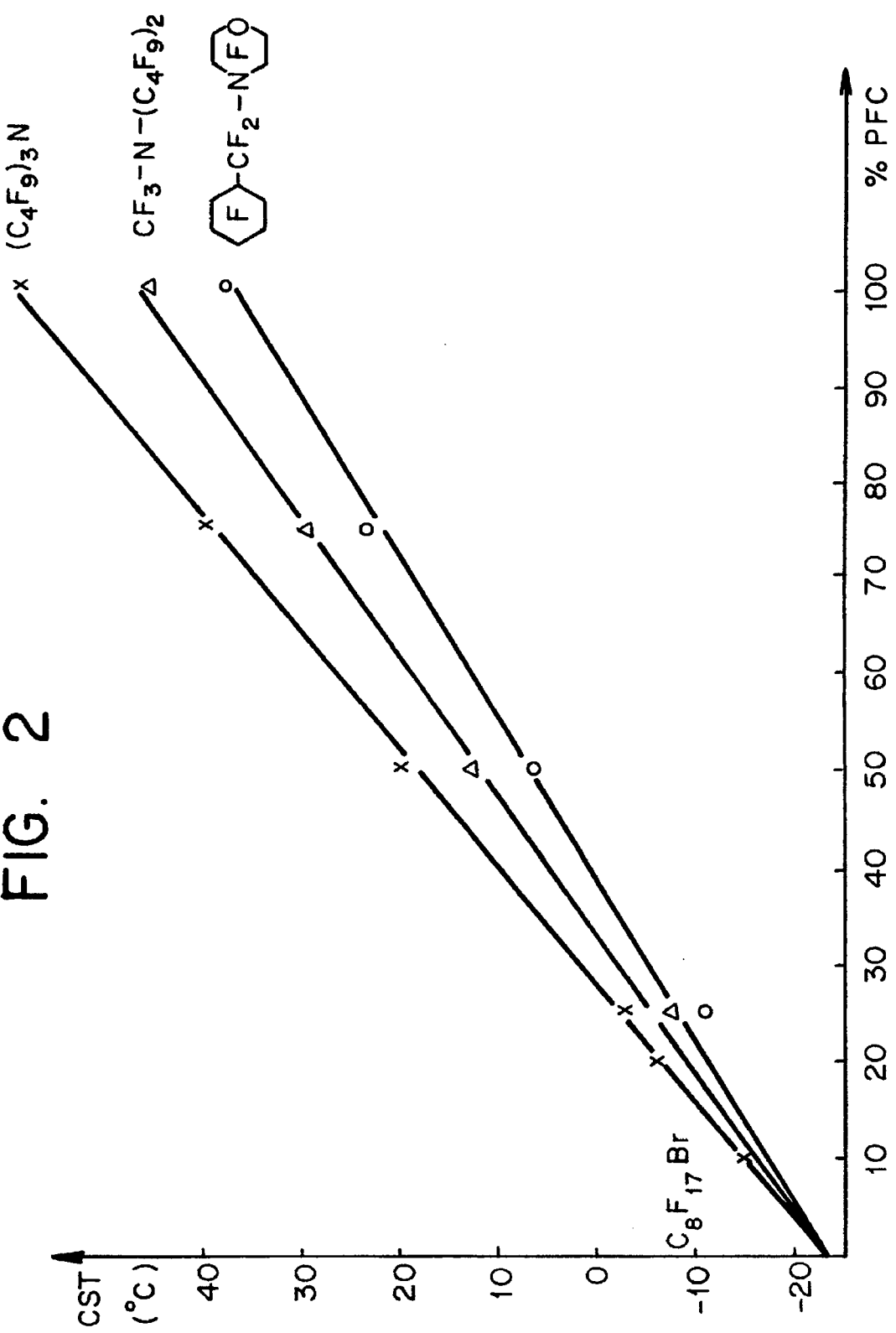
FIG. 2 is a diagram of the critical solubility temperatures of perfluorocarbon mixtures in n-hexane using F-octyl bromide as a starting point.

Some selected fluorocarbons and their $O_2$ solubility, their vapour pressure and their critical solubility temperature are shown in Table 1. Starting from these values, the desired characteristics for the penetration of the skin with the aid of a dermatological composition can be selected for mixtures of fluorocarbons.

TABLE 1

| Fluorocarbon | O₂ solubility [ml of O₂/100 ml of FC] | Vapour Pressure $P_{37°C.}$ [mm Hg] | CST [°C.] |
|---|---|---|---|
| Perfluorooctyl bromide | 50 | 14 | −24.5 |
| Perfluorodecalin | 40 | 12.5 | 22 |
| bis-F(butyl)ethene | 50 | 12.6 | 22.5 |
| F-cyclohexylmethyl-morpholine | 42 | 4 | 38.5 |
| F-tripropylamine | 45 | 18.5 | 43 |
| F-dihexyl ether | 45 | 2 | 59 |
| F-tributylamine | 40 | 1 | 59 |
| Perfluorodecalin-F-tributylamine 1:1 | 40 | 7 | 42 |
| Perfluorobutyl-tetrahydrofuran | 52 | 51 | 29 |
| F-methylcyclohexane | 57 | 180 | 8.2 |
| F-hexane | 58 | 414 | 20 |

EXAMPLE 1

50 ml of a 10% strength aqueous phospholipid solution (soya lecithin, 40% phosphatidylcholine (PC)) are homogenised with ice-cooling together with 80 g of a highly pure fluorocarbon mixture containing no H atoms (90% perfluorodecalin, 10% F-dibutylmethylamine, critical solubility temperature 26° C.) using an ultrasonic disintegrator until the particles have a mean diameter of 244 nm. The lamellar structure of the aggregates of fluorocarbon and phospholipid can be detected from $^{31}$P-NMR measurements by the typical signal width as well as from electron micrographs. The aggregate dispersion can be mixed with suitable alcohols (ethanol, propylene glycol, glycerol) for the purpose of sterilisation without problems and without affecting its stability. Addition of 30 ml of ethanol produces sterility, the resulting dispersion having the following composition:

```
62% w/v fluorocarbons
9.7% phospholipids
19% ethanol
```

The zeta potential of minus 61 mV verifies a negative surface charge produced by the phospholipids with an electrostatic stabilisation of the dispersion. After saturation with gaseous oxygen, the dispersion is incorporated into a non-interacting ointment base which is compatible with the asymmetric lamellar aggregates.

EXAMPLE 2

18 g of lyophilised phospholipid of the composition [30% PC, 30% PE (phosphatidylethanolamine), 31% PI (phosphatidylinositol)] are dissolved in 90 ml of sterilised water and treated with 16 ml of undenatured ethanol. Using a mechanical high-speed stirrer (Ultra-Turrax, 15,000 rpm), the dispersion is stirred and at the same time perfluorodecalin (CST 22° C.) is added successively to the stirring container which is temperature-controlled at 20° C. The crude dispersion is homogenised at 500 atm in an inert gas stream in a high-pressure homogeniser of the Manton Gaulin type. At the start of the last but one passage, a-tocopherol acetate is added to the dispersion to 0.1% to avoid autoxidation processes and as a scavenger for free radicals in the skin tissue.

The measurements carried out using the photon correlation spectrometer N-4 MD (Coultronics) confirm the presence of a unimodal particle size distribution and a mean particle diameter of 128 nm. Electron microscopy investigation using the "negative staining" method are in agreement with this. According to $^{31}$P-NMR investigations, the asymmetric lamellar aggregates are present in the unilamellar state with a zeta potential of minus 76 mV. The composition of the dispersion is

```
48% w/v perfluorodecalin
13% phospholipids
9% ethanol.
```

EXAMPLE 3

80 g of n-F-hexane, which is present in a mixture with its perfluorinated isomers (CST 20° C.), were mechanically preemulsified with 9.5 grams of egg yolk 3-sn-phosphatidylcholine in 47 ml of deionised and sterilised water under inert gas conditions with the addition of 0.2% dl-alpha-tocopherol to give a crude dispersion. The crude emulsion was homogenised in a pressure homogeniser at pressures of 500 atm under a suitable temperature regime and with checking of the particle sizes. The dispersion obtained has a medium viscosity and a particle diameter of 294 nm. After addition of 8 ml of propylene glycol, stability and sterility (microorganism count less than 100 microorganisms/g) were observed at room temperature in a long-term test. Dilution, e.g. in the preparation of lotions, is possible without problems without a change in important colloid-chemical parameters.

Investigations of the dispersion using a light microscope in polarised light indicate the presence of an isotropic single phase system, in which liquid-crystalline structures are non-existent.

EXAMPLE 4

In vivo detection of liposome penetration

A freshly isolated physiologically intact skin was fixed by its inside to an O₂ sensor (Clark electrode) and the epidermis wetted with an O₂-transporting dispersion containing asymmetric lamellar aggregates. Under these conditions, the electrode does not indicate an O₂ partial pressure. After a penetration period of 57 minutes, the aggregates had reached the dermal skin section in the measuring area of the electrode. The O₂ partial pressure rose to a value of 159 mm Hg. The penetration rate into the skin is dependent on the type and size of the aggregates.

We claim:

1. Dermatological agent for assisting the transport of oxygen into the skin, comprising asymmetric lamellar aggregates, comprising (a) phospholipid having a phosphatidylcholine content of 30% to 99% by weight; and (b) oxygen-laden fluorocarbon or fluorocarbon mixture, the amount of fluorocarbon being in the range from 0.2% to 100% weight/volume;

the aggregates having a skin penetration depending on the critical solubility temperature of the selected fluorocarbon or fluorocarbon mixture, and being present in a carrier which is suitable for dermatological use; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

2. Dermatological agent according to claim 1, wherein the lamellar aggregates have an asymmetric, three-layer, structure originating from their fluorocarbon core.

3. Dermatological agent according to claim 1, wherein the fluorocarbon is selected from the group consisting of aliphatic straight-chain fluoroalkanes, aliphatic branched fluoroalkanes, monocyclic fluorocycloalkanes, monocyclic fluoroalkyl-substituted fluorocycloalkanes, bicyclic fluorocycloalkanes, bicyclic fluoroalkyl substituted fluorocycloalkanes, perfluorinated aliphatic amines, perfluoroinated bicyclic amines, bis(perfluoroalkyl)ethenes, and mixtures thereof.

4. Dermatological agent according to claim 3, wherein the fluorocarbon is selected from the group consisting of perfluorodecalin, F-butyl-tetrahydrofuran, perfluorotributylamine, perfluorooctyl bromide, bis-fluoro(butyl)ethene and $C_6$–$C_9$-perfluoroalkanes.

5. Dermatological agent according to claim 1, wherein the amount of the fluorocarbon is in the range from 20% to 100% weight/volume.

6. Dermatological agent according to claim 1, wherein the amount of the fluorocarbon is in the range from 40% to 100% weight/volume.

7. Dermatological agent according to claim 1, wherein the amount of the fluorocarbon is in the range from 70% to 100% weight/volume.

8. Dermatological agent according to claim 1, wherein the phospholipid is selected from the group consisting of natural phospholipids, synthetic phospholipids, and the mixtures thereof, the concentration of the phospholipids being in the range from 0.5% to 20% by weight.

9. Dermatological agent according to claim 1, wherein the phosphatidylcholine is present in an amount from 60% to 90%.

10. Dermatological agent according to claim 1, wherein the lipid fraction used, in addition to phosphatidylcholine, lysolecithins are present in the concentration range from 0.1% to 5% by weight.

11. Process for the preparation of a dermatological agent for assisting the transport of oxygen into the skin, comprising the steps of emulsifying phospholipids having a phosphatidylcholine content of 30% to 99% by weight with an oxygen-laden fluorocarbon or fluorocarbon mixture, the amount of fluorocarbon being in the range from 0.2% to 100% weight/volume to produce asymmetric lamellar aggregates; and incorporating asymmetric lamellar aggregates having a particle size from 50 nm to 1000 nm obtained in this way into a dermatological carrier; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

12. Process according to claim 11, wherein the amount of fluorocarbon is in the range from 20% to 100% weight per volume;

the amount of phosphatidylcholine in the lipid fraction is in the range from 60% to 90%.

13. Process according to claim 12, wherein the amount of fluorocarbon is in the range from 40% to 100%.

14. Process according to claim 11, wherein the particle size is in the range from 120 nm to 820 nm.

15. Process according to claim 11, wherein the particle size is in the range from 140 nm to 400 nm.

16. In a method for controlling the supply of oxygen to the skin, the improvement which comprises applying to the skin a dermatological agent system comprising an asymmetric lamellar oxygen carrier, containing phospholipids having a phosphatidylcholine content of 30% to 99% by weight; and a fluorocarbon, the fluorocarbon being in the range from 0.2% to 100% weight/volume and penetration into the skin being controlled by means of the carrier structure of the phospholipid aggregates and the critical solubility temperature of the fluorocarbons; and the system being distributed in a dermatological carrier selected from the group consisting of ointment, cream, lotion, water, paste, powder, gel, and tincture; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

17. The method claim 16, wherein the system being applied to a dressing or a plaster.

18. The method claim 16, wherein the system being applied by means of a spray.

* * * * *